(12) United States Patent
Jerebko (10) Patent No.: US 9,449,403 B2
(45) Date of Patent: Sep. 20, 2016

(54) OUT OF PLANE ARTIFACT REDUCTION IN DIGITAL BREAST TOMOSYNTHESIS AND CT

(75) Inventor: Anna Jerebko, Hausen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 199 days.

(21) Appl. No.: 14/353,116

(22) PCT Filed: Oct. 19, 2011

(86) PCT No.: PCT/EP2011/068264
§ 371 (c)(1),
(2), (4) Date: Apr. 21, 2014

(87) PCT Pub. No.: WO2013/056733
PCT Pub. Date: Apr. 25, 2013

(65) Prior Publication Data
US 2014/0294138 A1    Oct. 2, 2014

(51) Int. Cl.
*A61B 6/00* (2006.01)
*G06T 11/00* (2006.01)
(Continued)

(52) U.S. Cl.
CPC ............ *G06T 11/003* (2013.01); *A61B 6/025* (2013.01); *A61B 6/502* (2013.01); *A61B 6/5258* (2013.01);
(Continued)

(58) Field of Classification Search
CPC ...... A61B 6/025; A61B 6/032; A61B 6/583; A61B 6/502; A61B 6/4233; A61B 6/5258; G06T 2207/10112; G06T 2207/30068; G06T 11/005; G06T 11/003; G06T 11/006; G01N 23/046; G01N 23/06; G01N 23/08; G01N 23/083
USPC ...................... 378/4, 18, 21, 23, 27, 37, 901
See application file for complete search history.

(56) References Cited

U.S. PATENT DOCUMENTS

| 5,872,828 A | 2/1999 | Niklason et al. |
| 7,548,640 B2 * | 6/2009 | Jeunehomme ............ G06T 5/50 382/132 |

(Continued)

FOREIGN PATENT DOCUMENTS

| WO | 9803115 A1 | 1/1998 |
| WO | 2009134970 A1 | 11/2009 |

OTHER PUBLICATIONS

Thomas Mertelmeier, et al., "Optimizing filtered backprojection reconstruction for a breast tomosynthesis prototype device", Siemens Medical Solutions, Erlangen, Proc. of SPIE vol. 6142, 61420 (2006); 2006.

(Continued)

*Primary Examiner* — Jurie Yun
(74) *Attorney, Agent, or Firm* — Laurence Greenberg; Werner Stemer; Ralph Locher (57) ABSTRACT

Reduction of artifacts in digital breast tomosynthesis and in computed tomography. Because of the limited angular range acquisition in DBT the reconstructed slices have reduced resolution in z-direction and are affected by artifacts. Out-of-plane blur caused by dense tissue and large masses complicates 3D visualization and reconstruction of thick slices volumes. The streak-like out-of-plane artifacts caused by calcifications and metal clips distort the true shape of calcification, an important malignancy predictor. Microcalcifications could be obscured by bright artifacts. The technique involves reconstructing a set of super resolution slices and predicting the "artifact-free" voxel intensity based on the corresponding set of projection pixels using a statistical model learned from a set of training data. The resulting reconstructed images are de-blurred and streak artifacts are reduced, visibility of clinical features, contrast and sharpness are improved, 3D visualization and thick-slice reconstruction is possible without the loss of contrast and sharpness.

14 Claims, 8 Drawing Sheets

(51) Int. Cl.
*A61B 6/02* (2006.01)
*G06T 7/00* (2006.01)

(52) U.S. Cl.
CPC ............. *G06T 7/0012* (2013.01); *A61B 6/583* (2013.01); *G06T 2207/10112* (2013.01); *G06T 2207/30068* (2013.01)

(56) References Cited

U.S. PATENT DOCUMENTS

| | | | |
|---|---|---|---|
| 8,233,690 | B2 | 7/2012 | Ng et al. |
| 8,340,388 | B2 * | 12/2012 | Rosenstengel ........ G06T 7/0012 378/37 |
| 2003/0194121 | A1 | 10/2003 | Eberhard et al. |
| 2009/0060310 | A1 | 3/2009 | Li et al. |
| 2009/0274354 | A1 | 11/2009 | Ng et al. |
| 2011/0013817 | A1 | 1/2011 | Medow |
| 2011/0229007 | A1 | 9/2011 | Jerebko |

OTHER PUBLICATIONS

Cristian Badea, et al., "A wavelet-based method for removal of out-of-plane structures in digital tomosynthesis", Department of Medical Physics, University of Patras; 1998.

Willi A. Kalender, et al. "Reduction of CT Artifacts Caused by Metallic Implants", 1987.

Jun Ge, et al., "Digital tomosynthesis mammography: Intra- and interplane artifact reduction for high-contrast objects on reconstructed slices using a priori 3D geometrical information", Department of Radiology, University of Michigan 2007.

Yiheng Zhang, et al., "Truncation Artifact and Boundary Artifact Reduction in Breast Tomosynthesis Reconstruction", Department of Radiology, University of Michigan, 2008.

Jun Ge, et al., "Digital tomosynthesis mammography Improvement of artifact reduction method for high-attenuation objects on reconstructed slices", Department of Radiology, University of Michigan, 2008.

Peter M. Joseph, "An Improved Algorithm for Reprojecting Rays trough Pixel Images", IEEE Transactions on Medical Imaging, 1983.

Robert L. Siddon, "Fast calculation of the exact radiological path for a three-dimensional CT array", Department of Radiation Therapy and Joint Center for Radiation Therapy, Harvard Medical School, Boston, 1985.

Yong Long, et al., "A 3D Forward and Back-Projection Method for X-Ray CT Using Separable Footprint", 10th International Meeting on Fully Three-Dimensional Image Reconstruction in Radiology and Nuclear Medicine; 2009.

Samuel Matej, et al. "Practical Considerations for 3-D Image Reconstruction Using Sphereically Symmetric Volume Elements" IEEE, 1996, p. 68-78.

Cyril Riddell, et al. "Rectification for Cone-Beam Projection and Backprojection", IEEE Transactions on Medical Imaging, vol. 25, No. 7, Jul. 2006.

Dev P. Chakraborty, et al. "Self-masking Subtraction Tomosynthesis", Radiology 1984, p. 225-229; 2003.

Tao Wu et al., "Voting strategy for artifact reduction in digital breast tomosynthesis", Med. Phys. 33 (7) Jul. 2006 , pp. 2461-2471.

Z. Kolitsi et al., "A method for selective removal of out-of-plane structures in digital tomosynthesis", Med. Phys. 20 (1), Jan./Feb. 1993, pp. 47-50.

D. N. Ghosh et al., "Selective plane removal in limited angle tomographic imaging", Med. Phys. 12 (1), Jan./Feb. 1985, pp. 65-70.

Gary H. Glover et al., "An algorithm for the reduction of metal clip artifacts in CT reconstructions", Med. Phys. 8 (6), Nov./Dec. 1981, pp. 799-807.

Bruno De Man et al.,"Distance-driven projection and backprojection in three dimensions", Physics in Medicine and Biology, Phys. Med. Bio. 49, (2004), pp. 2463-2475.

Andy Ziegler et al.,"Efficient projection and backprojektion scheme for spherically symmetric basis functions in divergent beam geometry", Med. Phys. 33 (12) Dec. 2006, pp. 4653-4663.

Colas Schretter, "A fast tube of response ray-tracer", Med. Phys. 33(12), 2006 pp. 4744-4748.

* cited by examiner

OUT OF PLANE ARTIFACT REDUCTION IN DIGITAL BREAST TOMOSYNTHESIS AND CT

BACKGROUND OF THE INVENTION

Field of the Invention

The present invention relates to the reduction of artifacts in digital breast tomosynthesis and in computer tomography.

Because of the limited angular range acquisition in Digital Breast Tomosynthesis the reconstructed slices have reduced resolution in z-direction and are affected by artifacts. The out-of-plane blur caused by dense tissue and large masses complicates three dimensional visualization and reconstruction of thick slice volumes. The streak-like out-of-plane artifacts caused by calcifications and metal clips distort the true shape of calcification that is regarded by many radiologists as an important malignancy predictor. Small clinical features such as micro calcifications could be obscured by bright artifacts.

An out-of-plane blur caused by dense tissue and large masses complicates three dimensional visualization and reconstruction of thick slabs from several slices computed as a maximum intensity projection or an average intensity projection. The artifact reduction algorithm that are commonly used in computer tomography imaging and often applied to tomosynthesis are not ideally suited to reduce artifacts in tomosynthesis images caused by dense tissue, metal clips and calcified anatomical structures, so-called calcifications. One class of algorithms can involve skipping projection images with extensive shadowing in the projections.

Another algorithm can involve segmenting out the objects causing the artifacts, such as a needle or other high contrast objects, and avoiding reconstruction using these pixels, as has been used in computer tomography. Streak artifact removal algorithm similar to those conventionally used in computer tomography technology are often not applicable to tomosynthesis due to the limited acquisition angle. Artifacts in digital breast tomosynthesis are caused by large calcifications and dense tissue. It is to be understood, that masking-out these anatomical structures prior to reconstruction is not possible, because dense tissue has an amorphous structure and exact location calcification in the projections is difficult to determine prior to reconstruction. Statistical outlier rejection methods do not remove all out of-plane blur created by large dense structures such as masses, dense tissue and even large calcifications. The reason is that due to the limited angular range in tomosynthesis the projections containing the correct intensity information do not necessarily constitute the majority and therefore could even be removed as outlier themselves. Most outlier detection methods are based on statistical tests, such as Grubbs, Pierce, Dixon's Q test or Chauvenet's criteria that are suitable for unimodal data sets. Due to the limited angular range in digital breast tomosynthesis the set of sample pixels that represent a projection of a voxel on the detector plane at various angles is often not unimodal. There is a cluster of pixels that reflect true attenuation of a voxel and there could be one or more clusters where it was obscured by a higher intensity structure. Statistical tests such as Grubbs', also known as the maximum normed residual test, are designed to detect outliers in a unimodal data set. The use of such criteria in small sets or where a normal distribution cannot be assumed is not recommended.

One of the most efficient ways of out-of-plane artifact suppression is the use of slice thickness filter. The unwanted side effect of this filter is blurring of small anatomical details such as micro calcifications over the total thickness of the slice. This filter does not remove out-of-plane blur caused by dense tissue and large masses, which complicates three-dimensional visualization and reconstruction of thicker slabs.

BRIEF SUMMARY OF THE INVENTION

It is an object of the present invention to reduce artifacts in a reconstructed image and/or a projection image. The object of the invention is achieved by a method for reconstructing and displaying tomography data comprising the step of emitting X-ray radiation through a matter to be analyzed in a plurality of different angles and detecting the X-ray radiation emitted into the matter to be analyzed in a plurality of different projections after the X-ray radiation has passed through the matter with a detector comprising an array of pixels, wherein each pixel generates a grey value based on the received radiation. A volumetric image or a set of projection images is generated based on the grey values acquired by the array of pixels. The step of reconstructing a volumetric image or a set of projection images comprises the step of ignoring or replacing grey values by comparing them with a stored statistical model of image data, wherein the statistical model of the image data is determined by analyzing a stored set of image information, e.g. from a plurality of patients and/or a phantom. The object of the invention is also achieved by an apparatus for reconstructing and displaying tomography data comprising an emitter emitting X-ray radiation through a matter to be analyzed in a plurality of different angles and a detector detecting the X-ray radiation emitted into the matter to be analyzed in a plurality of different projections after the X-ray radiation has passed through the matter, wherein the detector comprises an array of pixels, wherein each pixel generates a grey value based on the received radiation. A reconstructing device is adapted to reconstruct a volumetric image or at least one projection image based on the grey values in the acquired array of pixels by ignoring or replacing grey values by comparing them with a stored statistical model of image data. The apparatus further comprises a model generation device adapted to generate the statistical model of the image data by analyzing a stored set of image information, e.g. from a plurality of patients and/or a phantom. The apparatus may be configured such as is described below with respect to the method. The statistical model of the image data may be calculated based on a stored set of image information that are sample images generated by emitting X-ray radiation through the matter to be analyzed in a plurality of different angles and detecting the X-ray radiation emitted into the matter to be analyzed in a plurality of different projections after the X-ray radiation has passed through the matter with the detector comprising the array of pixels, wherein each pixel generates a grey value based on the received X-ray radiation. The volumetric image and/or at least one projection image is reconstructed based on the grey values in the acquired array of pixels. A statistical model of the image data may be generated by analyzing the volumetric image and/or at least one projection images. These steps may be performed by the model generation device.

The statistical model of the image data may reflect the statistical distribution parameters of grey values in acquired projections contributing to the construction of each voxel of a volumetric image or a pixel in reconstructed a projection image. The statistical parameters may comprise a mean value and a standard deviation. The model may comprise a standard deviation for each grey value. During image reconstruction the voxel may be calculated based on the sum of all corresponding projection pixels. However, in tomosynthesis reconstruction only a limited amount of projections is available and a large portion of them could be affected by artifacts. Therefore, statistical distribution parameters computed directly from projections pixels could be severally biased.

The invention proposes to predict the statistical distribution parameters based on models, which are derived from acquired images. A grey value of a projection pixel is ignored or substituted by a suitable value, if the grey value is does not satisfy the chosen statistical test, wherein the mean or median value is computed from the acquired projection pixel set and all the other distribution parameters are predicted using the pre computed model. Particularly, a grey value of a projection pixel is ignored or substituted by a suitable value, if the grey value is not within a pre-configurable range. Therefore, outliers can be removed more reliably. Due to the limited angular range in tomosynthesis, particularly in breast tomosynthesis a majority of the projections pixels may be contributing to the artifacts. The distribution of the grey values of the projection pixel is not unimodal, not a Gaussian distribution and not a Poisson distribution. Therefore, the present invention proposes to calculate the statistical model based on reconstructed images without artifacts which have been calculated beforehand. The model generation device may pre-compute the statistical model of the image data based on intensity distribution parameters without the presence of artifacts. Thereby, physical phantoms containing multiple inserts with attenuation properties of different tissues may be imaged, wherein the physical phantoms are scanned multiple times with a range of acquisition parameters and variable object thicknesses. Thereby, it can be assured that the statistical model covers a wide range of acquisition parameters and a wide range of tissue densities and thicknesses.

Alternatively or additionally, a data set of real patient images representing a range of image acquisition parameters, object thicknesses and/or radiographic density may be sampled. The majority of the reconstructed image voxels are artifact free, therefore a fitting a smoothed regression model to these data is equivalent to modeling 'artifact-free' distribution.

The model generation device may predict regression-based model parameters of the distribution of the artifact free projection values. Thereby, a more accurate statistical model can be provided. The step of generating image information may comprise the step of generating filtered back projections or iteratively reconstructing the image and/or involve a projection-tool-projection reconstruction method. The edge length of a voxel may be set approximately equal to the edge length of a pixel of the detector detecting said X-ray radiation. The length of the edges of a voxel may be set such that the voxel is an isotopic voxel. An isotopic voxel may be a cube. The edge length of a voxel may be set such that for all projection angles the voxel projects into an area being smaller than or essentially equal to the size of approximately one pixel of the acquired projection. It is assumed that for each voxel j of the volume to be reconstructed there exists a number of projections $N>=Max\_proj$, $N>0$, in which voxel j is imaged with a minimal amount of overlapping higher intensity voxels corresponding to the dense region intersection with the X-ray Rij. For each voxel j of the volume there exists a number of projections $M=Max\_prof-N$, $M \geq 0$, where the projection voxel j overlaps with projections of voxels which correspond to the objects of significantly higher density intersection with the same ray Rij. It is not known a priori if a majority or minority of projections produces artifacts for a particular voxel due to the non unimodal distribution of the grey values of the pixel. Theoretically, a clustering approach could be used to separate the cluster of projections causing the artifact for a particular voxel from the artifact-free projection cluster.

For example, the Dunn index aims to identify dense and well separated clusters. It is defined as the ratio between the minimal inter-cluster distances to the maximal intra-cluster distance. For each cluster partition, the Dunn index can be calculated based on the inter-cluster distance. Cluster analysis requires intensive computation and would significantly increase the total reconstruction time.

A simplified algorithm could be used to reduce the computation time. For example, a simple approach is to reduce each sample set of projection pixels corresponding to a particular voxel to a unimodal set.

A smoothed model of distribution parameters (such as mean and standard deviation) instead of calculated parameters for each mean intensity of a voxel, object thickness, electrode voltage, electrode current, volume coordinates (in case of non uniform noise distribution) may be used. The reason to use the model parameters instead of a calculated parameter is that the calculated distribution parameters would be biased for the voxels where artifacts are caused not by a few projections (minority) but by a large number of projections.

For sets where one or more data points do not satisfy a chosen statistical outlier detection criteria for unimodal distributions (such as Grubbs, Pierce, Dixon's Q test or Chauve net's criteria) with model distribution parameters, each outlier is iteratively removed until all data points satisfy the chosen statistical criteria for the view calculated mean.

Alternatively, another approach is to remove or replace all pixel values that do not satisfy the chosen statistical test in one step. This solution provides a faster reconstruction, since it does not involve recalculating the distribution parameters. In fact, only one distribution parameter is calculated, such as the mean intensity of the pixel. The other parameters that are more computationally expensive (such as standard deviation required for some statistically tests) are predicted using the smoothed model which is pre-computed off-line on a set of training images. The sorting and on-line calculation of distribution parameters (such as median, standard deviation and/or percentile ranges) is a computationally expensive operation that is used in other artifact-reduction procedures, and such operation is avoided by the present invention.

The particular advantage of the present invention is to pre-compute a statistical model of intensity distribution parameters without the presence of artifacts and to avoid on-line computation of these parameters for all voxels. This may be done, as mentioned before, by means of imaging physical phantoms containing multiple inserts with attenuation properties of different breast tissues, scanned multiple times with the full range of image acquisition parameters and by variable object thicknesses. Alternatively, a large dataset of real patient images representing the full range of image acquisition parameters, object thicknesses and densities could be sampled and used as a training set. The statistical model of intensity distribution parameters is then fitted to the data, for example using a regression method.

Some parameters need to be estimated for each particular image acquisition system. The minimal number of protection pixels remaining in the artifact-free set has to be estimated. Further, the regression-based model parameters of the distribution of the artifact-free projection pixel value have to be estimated. For example, distribution parameters for each set of projection pixel values contributing to reconstruction of a particular voxel are predicted based on the mean value of all the corresponding projection pixels, object thicknesses, electrode voltages, electrode currents and/or volume coordinates. Further, the weighting coefficients for statistical outlier detection tests are estimated.

The invention suggests the following method for automatic parameter optimization for each particular system. In an interactive adjustment the parameters above could be selected by a human, such as a radiologist on a training set of images, such that all the clinically significant features (micro calcifications, masses, mass speculations, Cuper ligaments etc.) are imaged with the highest possible contrast. In an automatic adjustment the parameters are adjusted by maximizing the contrast and edge sharpness in a set of reconstructed clinical features, such as micro calcifications, masses and/or mass speculations.

A reference reconstruction method (such as filtered back projection or an iterative reconstruction with a large number of iterations to ensure visualization of all clinically significant features) is used to reconstruct a set of patient images. A human observer manually outlines or segments clinically significant features in each reconstructed patient image. The system parameters are then chosen to maximize the contrast of the faintest clinical features. An interactive final step could be used for the adjustment of the parameters to the preferences of the human observers.

The reconstructing device may be adapted to reconstruct a slice having a thickness of one voxel and to generate a slab that comprises a plurality of slices. The step of generating a slab may comprise generating an average projection, generating an integral projection, generating a maximum intensity projection, generating a linear combination of the average projection and/or integral projection and/or maximum intensity projection perpendicular to the slice plane or coinciding with one or more of the acquired projection angles, generating a non-linear combination of the average projection and/or integral projection and/or maximum intensity projection perpendicular to the slice plane or coinciding with one or more of the required projection angles.

The slabs may be displayed on a display. The radiologist may select a region of the slab. In this region, a slice having a higher resolution than the slab may be shown as a region of interest.

A regular filtered back projection method may be modified in order to incorporate the artifact reduction scheme. Instead of reconstructing slices with a thickness of S, wherein clinical slice thicknesses from approximately 1 mm to approximately 2 mm are used, the present invention suggests to reconstruct slabs consisting of several thin slices with the total thickness S. Each slab contains isotopic voxels with the size equal to the pixel size p of the acquired projections. The number of thin slices within a slab equals approximately to S/p. The goal is to ensure that each isotopic voxel (cube-like voxel) projects into approximately one pixel of each acquired projection.

This ensures that the statistical distribution parameters as required in the artifact reduction step, of a set of pixel intensities from acquired projections correspond to one isotopic voxel without incorporating intensities of a larger number of neighboring pixels. A bilinear interpolation on the detector plane could be used because each forward projected voxel can overlap with neighboring pixels on the detector plane, e.g. four neighboring pixels.

In a regular filtered back projection method the present invention suggests for reconstructing each voxel to compute a sum of filtered and bilinear interpolated pixels of all projections where this voxel was imaged.

The present invention suggests using the above artifact reduction method applied on each isotopic voxel constituting the slab before computing the sum of the projection values.

Although the projection could be filtered prior to reconstruction, the present invention suggests removing the slice thickness filter or adjusting it to the thickness p, not S. After the artifact reduction step, the slab could be collapsed into a slice with thickness S. Thicker slices may be generated by performing average intensity projection or a maximum intensity projection of a slab of thin slices in the direction orthogonal to the slice plane (detector plane). The thick slice could be obtained by projecting each set of thin slices corresponding to one thick slice on a detector plane with the angle of one of the acquired projections. The projections could be computed using the Siddon method, Joseph method, a distance-driven projector, a separate-footprint projector or any other way of ray casting or forward projecting technique. The full thin-slice volume does not need to be kept in the memory. Only one set of slab slices at a time is required to compute one slice of a thicker slice volume. The resulting slices of thick-slice volume are kept in the memory, stored on a hard disk or another medium and/or displayed for viewing.

The reconstruction device may perform the step of generating a projection image that comprises at least one of the following steps: generating a set of forward projections of the reconstructed digital breast tomosynthesis volume for visualizing a rotating mammogram, pre-computing forward projections using a set of sequential viewing angels within the order of magnitude of the maximum tomosynthesis angular range, generating an average projection, generating an integral projection, generating a maximum intensity projection, generating a linear combination of the average projection and/or integral projection and/or maximum intensity projection perpendicular to the slice plane or coinciding with one or more of the acquired projection angles, generating a non-linear combination of the average projection and/or integral projection and/or maximum intensity projection perpendicular to the slice plane or coinciding with one or more of the acquired projection angles.

A mammogram simulated from digital breast tomosynthesis data could be useful in clinical practice because they keep the look and feel of screening mammographic images, such as full field digital mammography images, while avoiding additional radiation dose needed for acquisition of a real full field digital mammography image in addition to already acquired digital breast tomosynthesis data.

A simulated mammogram allows reconstructing originally acquired projections with a higher level of detail, signal to noise ratio and contrast to noise ratio. This is achieved because each projection is reconstructed taken into account information from all the acquired projections. The projections could be reconstructed to simulate a rotating three-dimensional mammogram by projecting on the detector orthogonal to the ray from the radiation source through the rotation set (different compared to the acquisition geometry). A sequence of projections reconstructed this way forms a three-dimensional rotating mammogram view that efficiently renders three-dimensional information and allows removing or shifting occlusions by rotating the three-dimensional mammogram. Such representation of digital breast tomosynthesis data limits the amount of images to be browsed, transmitted and stored to a chosen number of discrete viewing angles independently of the breast thickness. Although a three-dimensional rotating mammogram could be simulated from regular reconstructed digital breast tomosynthesis volume, the quality thereof is limited not only by the angular range of the digital breast tomosynthesis itself but also by the reconstructed slice thickness. The reconstructed voxels are highly anisotropic (e.g. approximately 0.085 mm×0.085 mm×1 mm) which results in additional blurring of defining clinically significant features such as micro calcification and speculations of masses. Therefore, the present invention proposes to forward project all isotopic voxels in thin slices of a slab reconstructed with the above isotopic filtered back projection reconstruction with the artifact reduction in the memory. The forward projection could be ray-driven or voxel driven. The resulting simulated projections should contain the accumulated sum for average intensity projection or maximum intensity projection or a non-linear or linear combination of forward projections of all the isotopic voxels from the slabs.

It is also possible to reconstruct three-dimensional rotating mammograms directly from acquired digital breast tomosynthesis projections, skipping the step of digital breast tomosynthesis volume reconstruction and thus avoiding the problem of forward projecting and an isotopic voxel. Each pixel value in reconstructed projections corresponds to the ray integral for average intensity projection or maximum over the ray for maximum intensity projection or a combination of those of the object intensity function sampled with step size lesser or equal to the projection pixel size. Each sample of the object density function V contains the integrated artifact-free set of projection pixel values Pf corresponding according to the system acquisition geometry to the three-dimensional coordinates of the sample in the object space. The set of original projection pixel values P is obtained from original acquirable projections or filtered projections by projecting the three-dimensional voxel sample V onto the detector. The artifact-free set Pf is then obtained from the original set P by applying the artifact reduction scheme described herein.

The present invention is also directed to a computer program product comprising code means adapted to execute the steps according to the above described method, when loaded into a processor.

BRIEF DESCRIPTION OF THE DRAWINGS

The invention is described with reference to an exemplary non-limiting embodiment shown in the figures.

DESCRIPTION OF THE INVENTION

The invention is now explained with reference to the figures in order to illustrate an exemplary and non-limiting embodiment thereof.

Figure 1:
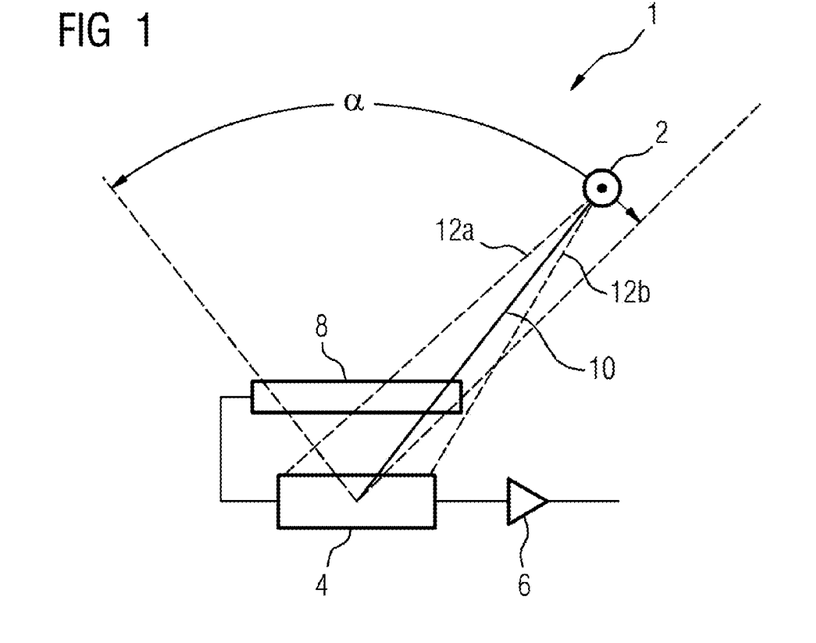
FIG. 1 shows an exemplary modality used by the present invention.
Figure 2:
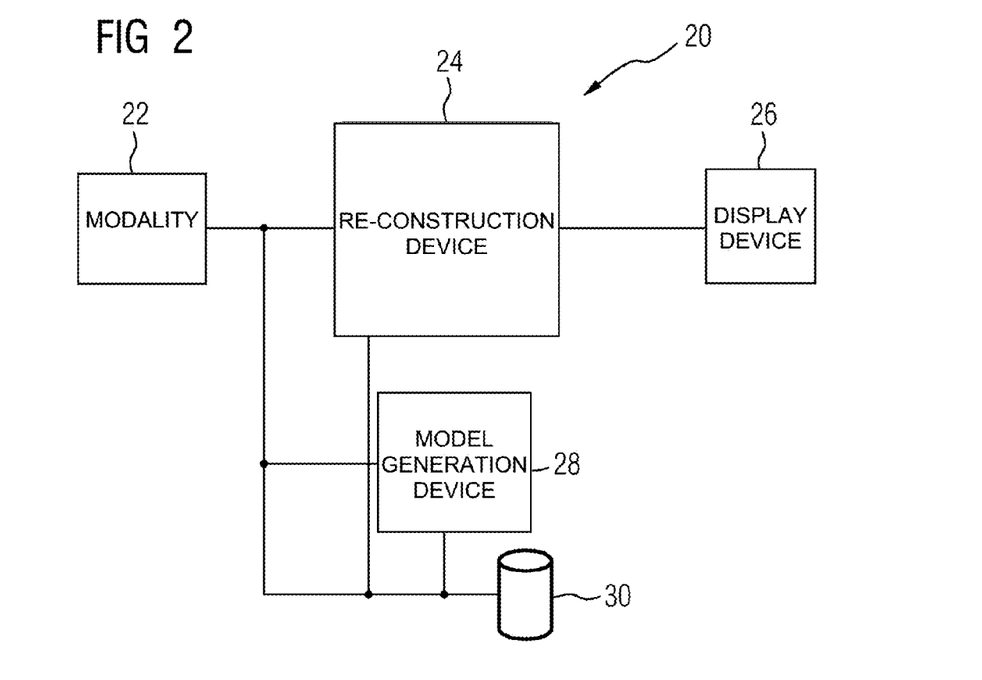
FIG. 2 shows a schematic diagram of an inventive apparatus.

FIG. 1 show an exemplary modality 1 which is used for digital breast tomography. The modality 1 comprises a radiation source that is arranged on a gantry 10. The radiation source 2 emits a beam 12a, 12b to the detector 4. The breast is arranged on the detector 4. The breast is compressed by a compression plate 8 that is linked with the detector plate. The gantry 10 and the X-ray radiation source 2 are pivot able within the limited angle range α. After positioning the radiation source 2 under a pre-determined angle, X-ray radiation is emitted by the radiation source 2 and the array of pixels of the detector 4 acquire a projection that is output via an amplifier 6. Thereafter, a further projection image is acquired, after the radiation source 2 is positioned under a different angle with respect to the breast and the detector 4. FIG. 2 shows an exemplary apparatus 20 for reconstructing and displaying tomography data. A modality 22 generates a plurality of projection images which are transferred to a reconstruction device 24. The reconstruction device 24 reconstructs a volumetric image or a set of projection images based on the acquired grey values of the array of pixel by ignoring or replacing grey values by comparing them with a stored statistical model of image data. The volumetric image or the projection image is output on a display device 26. The reconstruction device 24 retrieves the statistical model from a storage unit 30. The apparatus 20 for reconstructing and displaying tomography data further includes a model generation device 28 that generates a statistical model of the image data by analyzing a stored set of image information from a plurality of patients or a phantom. The statistical model may comprise a standard deviation associated to a mean value.

Figure 3:
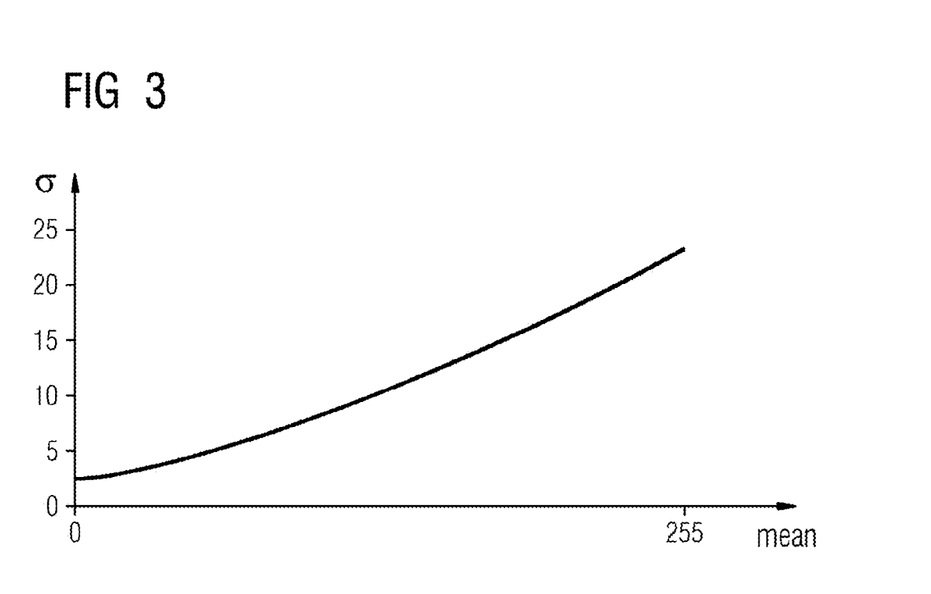
FIG. 3 shows an exemplary statistical model.

FIG. 3 shows a plot of the mean value versus the standard deviation. In other words, a mean value of zero corresponds to a standard deviation of approximately 2.5 whereas, a mean value of 225 corresponds to a standard deviation of approximately 25. The plot according to FIG. 3 can be determined by the method described above, e.g. by scanning a phantom or by investigating a plurality of patient images.

Figure 4:
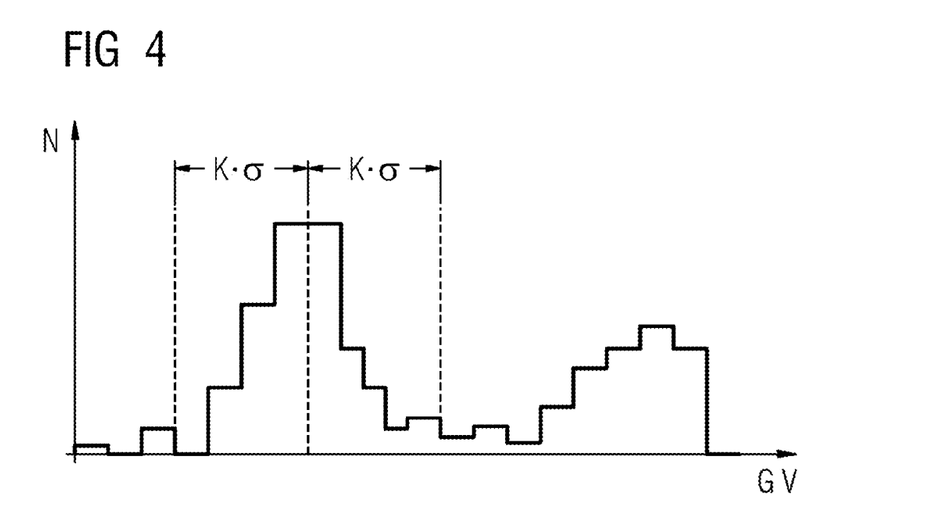
FIG. 4 shows the application of the statistical model when reconstructing a volumetric image or a projection.

FIG. 4 shows a plot of the intensity of different projection pixels that are assigned to the same voxel. The x axis indicates the grey value, whereas the y axis indicates the number of pixels having approximately the same grey value. FIG. 4 is a histogram representation that shows a bimodal curve.

Figure 5:
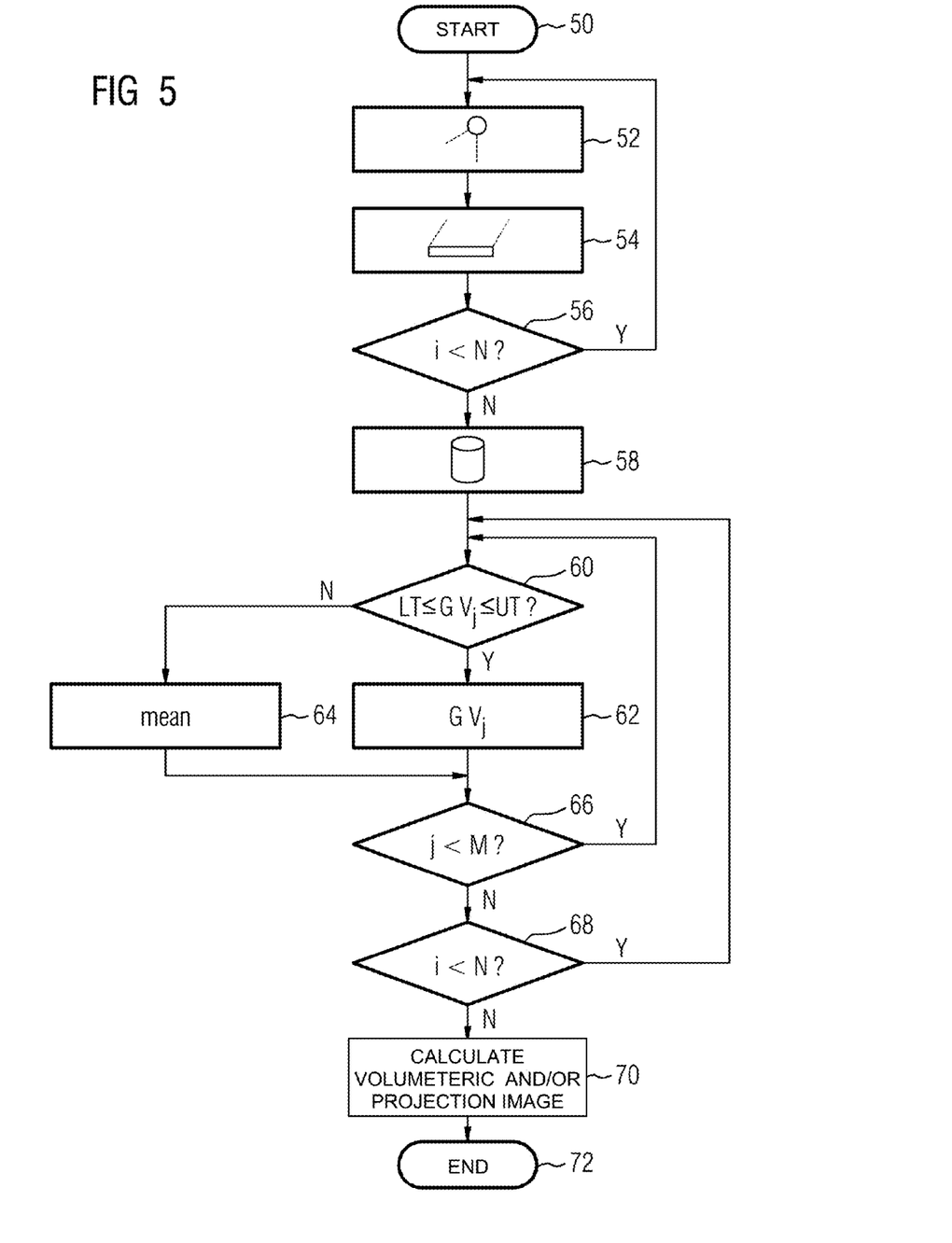
FIG. 5 shows an exemplary method for reconstructing a volumetric image or a projection image applying the statistical model of image data.

The statistical model indicates that the lower grey values represent the expected or true grey value. Therefore, only grey values satisfying statistical model are used by the reconstruction device 24 to reconstruct the image. All other grey values may be ignored or substituted by the mean value. Reference is made to FIG. 5. FIG. 5 shows a method according to the present invention. The method starts that step 50. In step 52 X-ray radiation is emitted, which passes the body of the patient. In step 54 a detector having an array of pixel detects the X-ray radiation. Thereby, the attenuation of the body tissue which the X-ray radiation passed can be determined. In step 56 it is determined, whether all necessary projections have been imaged. If not all necessary projections have been imaged yet, steps 52 and 54 are repeated until all projections are determined, wherein the body tissue is subjected to X-ray radiation under a different angle. In step 58 the N projections are stored in a data base.

In step 60 it is determined whether the grey value GVj is larger or equal than a lower threshold LT and smaller or equal than an upper threshold UT. The lower threshold LT and the upper threshold TH are determined from a statistical model that has been described with respect to FIGS. 3 and 4.

If the grey value GVj is within the before mentioned allowed range between the lower threshold LT and upper threshold UT, the grey value GVj is used in step 62 for determining the voxel, e.g. by a maximum intensity projection or a mean intensity projection.

If the grey value GVj is not within the allowed range, step 64 outputs the mean value of the statistical model as the grey value of the respective pixel of the respective projection. This method ensures that the allowed mean value is used for determining the voxel value, e.g. by maximum intensity projection or mean intensity projection.

Step 66 ensures that steps 60, 62 and 64 are repeated over all M pixels of a projection. Step 68 ensures that steps 60, 62, 64 and 66 are repeated for all N projections. If all M pixels in N projections have been examined and the corresponding voxel value of their volumetric representation calculated is calculated in step 70. Step 70 calculates the volumetric image and/or projection image. The procedure ends in step 72.

Figure 6:
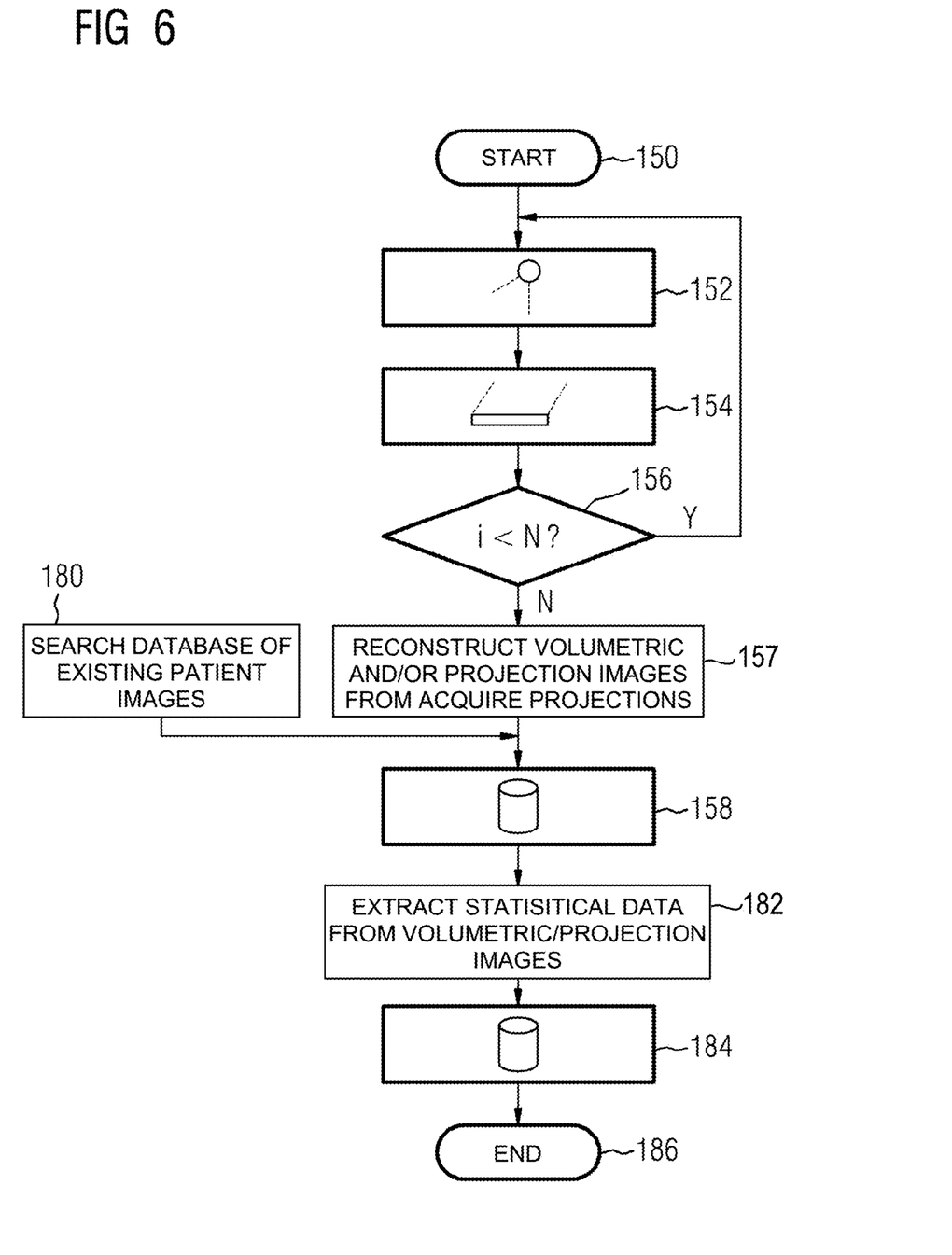
FIG. 6 shows a schematic diagram illustrating the generation of the statistical model of image data.

Reference is made to FIG. 6 showing an illustrative method for generating the statistical model. The method commences in step 150. Steps 152, 154, 156 corresponds to steps 52, 54 and 56, respectively of FIG. 5. For the sake of brevity and clarity the description thereof is not repeated. Steps 152, 154 and 156 are performed over variety of different tissue types and tissue thicknesses. Further, the parameter of the X-ray apparatus, such as electrode voltage, electrode current etc., may be changed wherein one phantom is imaged by a plurality of different parameters of the X-ray apparatus. It is to be understood that instead of a phantom, patients may be used for obtaining the acquired projections for generating the volumetric images. In step 157 volumetric images and/or projection images are reconstructed from the acquired projections.

The reconstructed volumetric images and/or projection images are stored in a database in step 158. The database may also be fed with patient data that has been determined to be relevant in step 180. In other words, step 180 searches a database of existing patient images for relevant images and forwards this information to step 158 in which the relevant image data is stored in a database.

Step 158 is followed by step 182 in which statistical data as shown in FIG. 3 is extracted from the volumetric images and projection images in the database. Step 182 may extract statistical distribution parameters such as mean values, standard deviation and the like as has been described above with respect to the inventive method. The statistical models are stored in step 184 in a database comprising a statistical model of image data. The method ends in step 186.

In the follow figures, the grey values are inverted for reasons of representation. I.e. a black pixel in the figures actually represents a high grey value and verse visa.

Figure 7:
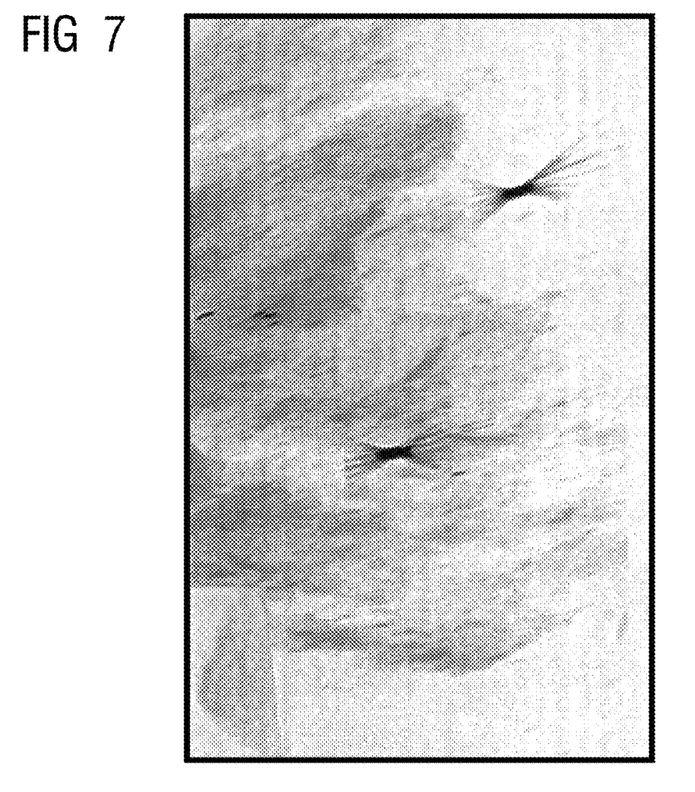
FIG. 7 shows a prior art image having artifacts.

FIG. 7 shows an oblique maximum intensity projection visualizing out-of-plane-artifacts caused by dense tissue and calcifications in a breast volume reconstructed with a filtered back projection method.

Figure 8:
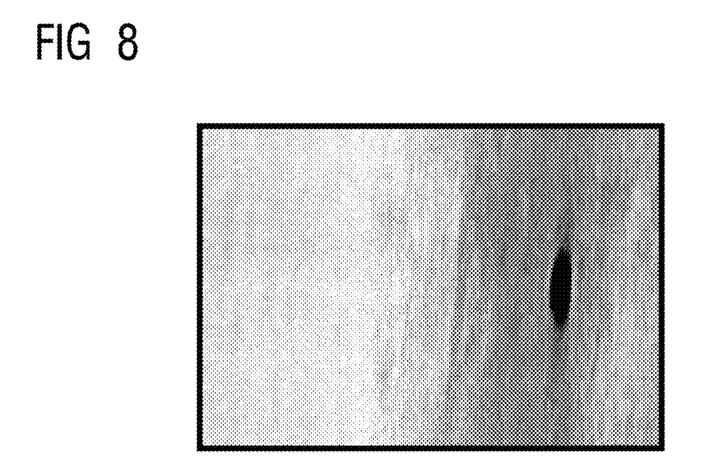
FIG. 8 shows a coronal slice without artifact reduction.

FIG. 8 shows a one millimeter thick coronal slice computed without artifact reduction using the original filtered back projection algorithm.

Figure 9:
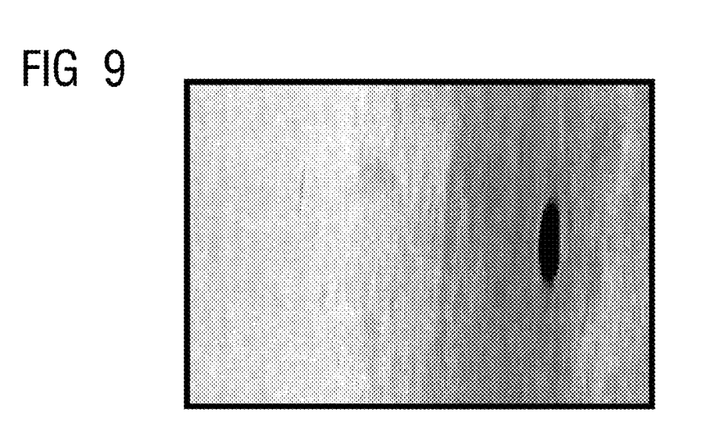
FIG. 9 shows a coronal slice computed with artifact reduction.

FIG. 9 is an example of a one millimeter thick coronal slice computed with the artifact reduction according to the present invention.

Figure 10:
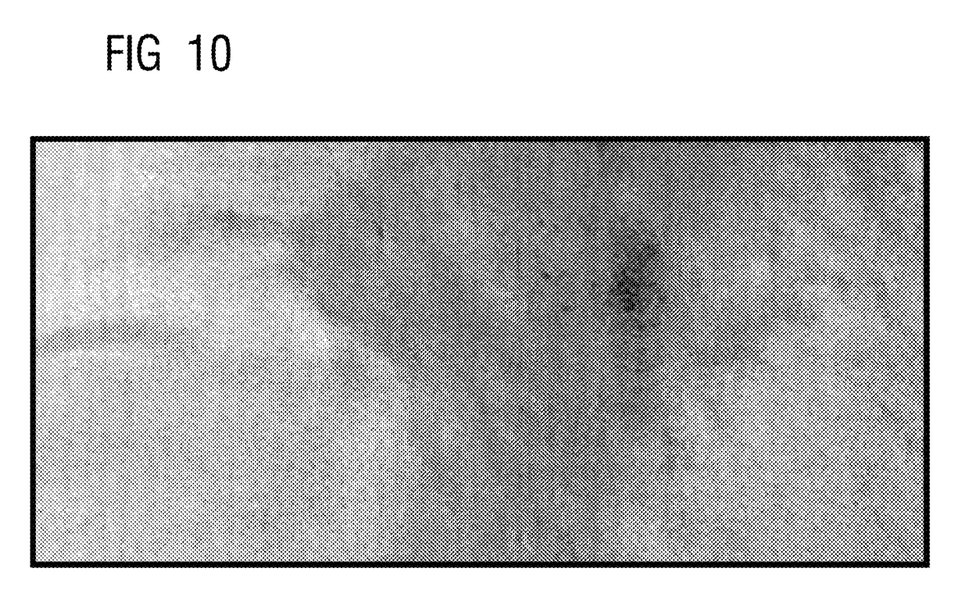
FIG. 10 shows an axial slab reconstructed without artifact reduction.

FIG. 10 shows a two millimeter thick maximum intensity projection axial slab reconstructed with the original forward back projection without artifact reduction.

Figure 11:
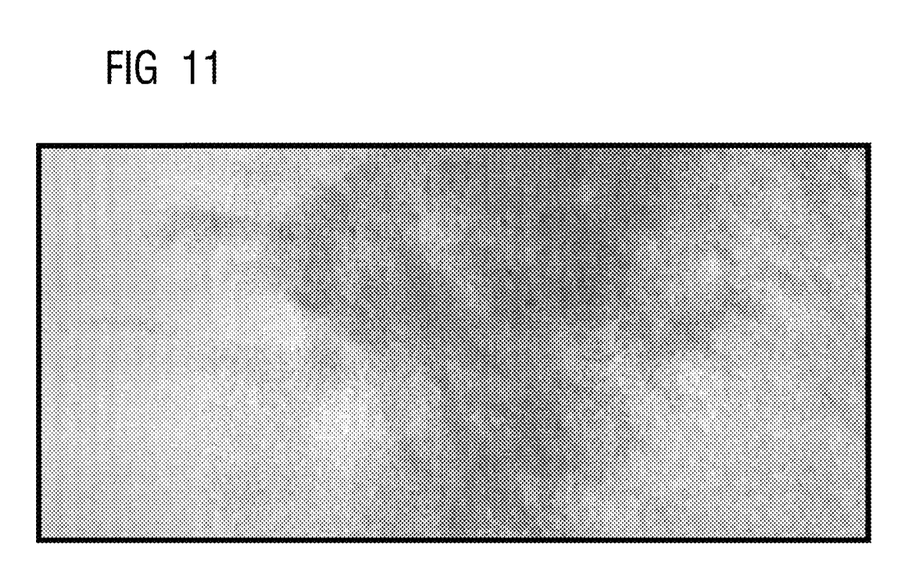
FIG. 11 shows an axial slab with artifact reduction.

FIG. 11 shows a two millimeter thick maximum intensity projection axial slab reconstructed with artifact reduction.

Figure 12:
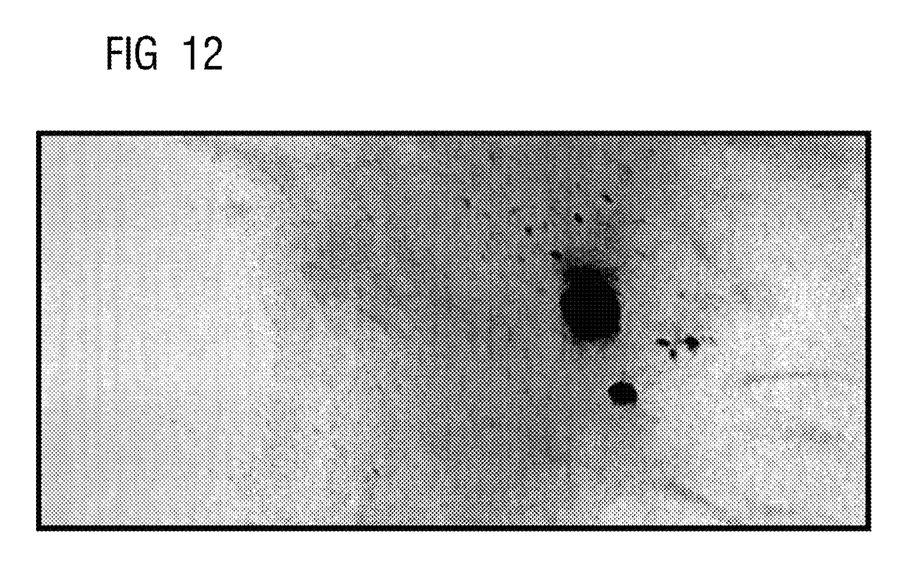
FIG. 12 shows a maximum intensity projection computed without artifact reduction.

FIG. 12 shows a maximum intensity projection computed from the volume reconstructed with the original filtered back projection method.

Figure 13:
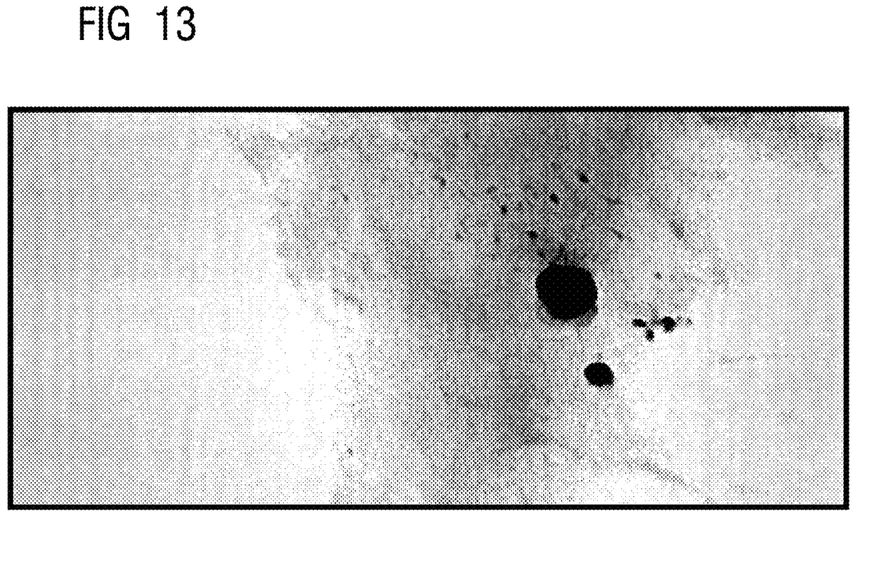
FIG. 13 is a maximum intensity projection with artifact reduction.

FIG. 13 shows a maximum intensity projection computed from the volume reconstructed with the artifact reduction method.

The present invention reconstructs a set of thin slices with isotropic voxels with a size approximately equal to the projection pixel size and performs an outlier removal or artifact reduction step on isotropic voxels. The pixel intensity and noise distribution parameters of projection pixel intensity samples are modeled corresponding to each voxel in the object space using a set of training images representing the full range of image acquisition parameters, object thicknesses and/or densities. The artifact-free pixel intensity and/or noise distribution parameters are predicted for each voxel in 15 the new test or patient images based on available image acquisition parameters, mean intensities of the projection pixel sample corresponding to each voxel using the learned model. Predicted artifact-free pixel intensity parameters and/or noise distribution parameters are used for each voxel in a statistical outlier removal by an artifact reduction algorithm.

A weighting factor in a statistical outlier removal test is optimized based on maximizing the contrast-to-noise ratio in a set of clinical features marked in the training images.

A statistical test with distribution parameter model is used that is predicted by using the trained model and the weighting factor determined by the above-mentioned method on the thin-slice isotropic voxels and then by computing thicker slices by average or maximum intensity projection of a slab of thin slices in the direction orthogonal to the slice plane, i.e. detector plane or with one of the acquisition angles. The full thin-slice volume does not need to be kept in the memory. Only one set or slab of slices at a time is required to compute one slice of a thicker slice volume. The set of slices belonging to a slab could be kept in the memory or alternatively only one thin slice at a time could be kept in the memory and added to the thick slice incrementally. Slices of thick-slice volume are kept in the memory and/or stored on a hard drive or another medium and/or displayed for viewing.

A thick-slice volume is obtained by performing the step above but projecting each set of thin-slices corresponding to one thick slice on the detector plane with the angle of one of the acquired projections. The projections of the digital breast tomosynthesis volume could be computed using a Siddon method, a Joseph method, a distance-driven projector, a separable-footprint projector or any other ray casting or forward projection technique. The present invention provides the advantage that the reconstructed image is deblurred and streak artifacts are reduced. Further, thick-slice reconstruction or slabbing is possible without the loss of contrast or sharpness. Three-dimensional visualizations and simulated forward projections are possible. An additional efficient noise control through filtering or the use of the prior functions is possible while the boundaries are preserved. Visibility of clinical features is improved and a higher contrast to noise ratio is achieved. The invention proposes a method for out-of-plane artifact reduction in digital breast tomosynthesis reconstruction. Because of the limited angular range acquisition in Digital Breast Tomosynthesis the reconstructed slices of prior art methods have reduced resolution in z-direction and are affected by artifacts. The out-of-plane blur caused by dense tissue and large masses complicates three dimensional visualization and reconstruction of thick slices volumes with prior art methods. The streak-like out-of-plane artifacts caused by calcifications and metal clips distort the true shape of calcification that is regarded by many radiologists as an important malignancy predictor. Small clinical features such as micro calcifications could be obscured by bright artifacts.

The inventive technique involves reconstructing a set of super resolution slices and predicting the 'artifact-free' voxel intensity based on the corresponding set of projection pixels using a statistical model learned from a set of training data.

Experiments show that the resulting reconstructed images are de-blurred and streak artifacts are reduced, visibility of clinical features, contrast and sharpness are improved, three dimensional visualization and thick-slice reconstruction is possible without the loss of contrast and sharpness.

LIST OF REFERENCE NUMERALS 1 modality
2 radiation source
4 detector
6 amplifier
8 compression plate
10 gantry
12a, 12b X-ray
20 apparatus for reconstruction and displaying tomography data
22 modality
24 reconstruction device
28 model generation device
30 storage unit
50 start
52 emitting X-ray radiation
54 X-ray detection
56 all projection imaged?
58 storing database
60 grey value within allowed range
62 use grey value
64 use mean value
66 all pixels of the projection verified?
68 all projections verified?
70 calculating volumetric images or projection images
72 end
150 start
152 emitting radiation
154 X-ray detection
156 all projection imaged
157 calculating volumetric images or projection images
158 storing projections and database
180 searching existing imagers
182 calculating statistical model
184 storing statistical model
186 end

The invention claimed is:

1. A method of reconstructing and displaying tomography data, comprising the following steps:
emitting X-ray radiation through a matter to be analyzed in a plurality of different angles;
detecting the X-ray radiation emitted into the matter to be analyzed in a plurality of different projections after the X-ray radiation has passed through the matter with a detector having an array of pixels, wherein each pixel generates a grey value based on the received X-ray radiation; and
reconstructing a volumetric image or at least one projection image based on the grey values acquired by the array of pixels,
thereby ignoring or replacing grey values by comparing the respective grey values with a stored statistical model of image data, the statistical model of the image data being determined by analyzing a stored set of image information.

2. The method according to claim 1, which comprises calculating the statistical model of the image data based on a stored set of image information that are sample images generated by the following steps:
emitting X-ray radiation through the matter to be analyzed at a plurality of different angles;
detecting the X-ray radiation emitted into the matter to be analyzed in a plurality of different projections after the X-ray radiation has passed through the matter with the detector having the array of pixels, wherein each pixel generates a grey value based on the received X-ray radiation;
reconstructing a volumetric image and/or a set of projection images based on the grey values acquired in the array of pixels; and
generating a statistical model of the image data by analyzing the volumetric image and/or set of projection images.

3. The method according to claim 1, wherein the statistical model of the image data reflects the statistical distribution parameters of grey values in acquired projections contributing to the reconstruction of each single voxel of a volumetric image or a pixel in reconstructed projection images.

4. The method according to claim 1, further comprising at least one of the following steps:
precomputing the statistical model of the image data based on intensity distribution parameters without the presence of artifacts;
imaging physical phantoms containing multiple inserts with attenuation properties of different tissues, wherein the physical phantoms are scanned multiple times with a range of image acquisition parameters and variable object thicknesses.

5. The method according to claim 1, which comprises generating the statistical model of the image data by sampling a data set of real patient images representing one or more of a range of image acquisition parameters, object thicknesses, and/or radiographic densities.

6. The method according to claim 1, which comprises generating the statistical model of the image data by predicting a parameter model of the distribution of an artifact free projection pixel value by way of regression analysis.

7. The method according to claim 1, which comprises generating image information by generating filtered back projections or iteratively reconstructing the image and/or carrying out a projection-to-projection reconstruction method.

8. The method according to claim 1, which comprises generating image information by carrying out at least one of the following steps:
- setting an edge length of a voxel approximately equal to an edge length of a pixel of the detector detecting the X-ray radiation;
- setting a length of the edges of a voxel such that the voxel is an isotropic voxel;
- setting the edge length of a voxel such that for all projection angles the voxel projects into an area being smaller than or substantially equal to a size of approximately one pixel of the acquired projection.

9. The method according to claim 1, which comprises generating image information by at least one of the following steps:
- reconstructing a slice having a thickness of one voxel;
- generating a slab that comprises a plurality of slices.

10. The method according to claim 9, wherein the step of generating a slab comprises at least one of the following steps:
- generating an average projection;
- generating an integral projection;
- generating a maximum intensity projection;
- generating a linear combination of the average projection and/or integral projection and/or maximum intensity projection perpendicular to a slice plane or coinciding with one or more of the acquired projection angles;
- generating a nonlinear combination of the average projection and/or integral projection and/or maximum intensity projection perpendicular to the slice plane or coinciding with one or more of the acquired projection angles.

11. The method according to claim 9, wherein the generating step comprises generating a plurality of slabs, and the method further comprises:
- displaying the slabs on a display; and
- displaying a slice having a higher resolution than the slab for a region of interest.

12. The method according to claim 1, which comprises generating a projection image by carrying out at least one of the following steps:
- generating a set of forward projections of a reconstructed digital breast tomosynthesis volume for visualizing a rotating mammogram;
- pre-computing forward projections using a set of sequential viewing angles within an order of magnitude of a maximum tomosynthesis angular range;
- generating an average projection;
- generating an integral projection;
- generating a maximum intensity projection;
- generating a linear combination of the average projection and/or integral projection and/or maximum intensity projection perpendicular to a slice plane or coinciding with one or more of the acquired projection angles;
- generating a nonlinear combination of the average projection and/or integral projection and/or maximum intensity projection perpendicular to the slice plane or coinciding with one or more of the acquired projection angles.

13. A computer program product, comprising computer-executable code stored in non-transitory form and configured to execute the method steps according to claim 1 when loaded into a processor.

14. An apparatus for reconstructing and displaying tomography data, comprising:
- an emitter emitting and projecting X-ray radiation through a matter to be analyzed in a plurality of different angles;
- a detector detecting the X-ray radiation emitted into the matter to be analyzed in a plurality of different projections after the radiation has passed through the matter;
- said detector including an array of pixels and each pixel generating a grey value based on the received X-ray radiation;
- a reconstruction device configured to reconstruct a volumetric image or at least one projection image based on the grey values acquired in the array of pixels by ignoring or replacing grey values by comparing them with a stored statistical model of image data; and
- a model generation device configured to generate the statistical model of the image data by analyzing a stored set of image information.

* * * * *